US005518504A

United States Patent [19]
Polyak

[11] Patent Number: 5,518,504
[45] Date of Patent: May 21, 1996

[54] IMPLANTABLE SPHINCTER SYSTEM UTILIZING LIFTING MEANS

[75] Inventor: Mark Polyak, New York, N.Y.

[73] Assignee: American Medical Systems, Inc., Minnetonka, Minn.

[21] Appl. No.: 174,531

[22] Filed: Dec. 28, 1993

[51] Int. Cl.⁶ ........................................ A61F 2/48
[52] U.S. Cl. .................. 623/14; 623/12; 623/26; 128/DIG. 25; 600/31; 600/37
[58] Field of Search ................. 600/29–31, 37; 128/DIG. 25, 887, 831; 623/14, 12, 26

[56] References Cited

U.S. PATENT DOCUMENTS 3,815,576  6/1974  Balaban ..................... 623/12 X
4,118,805  10/1978  Reimels ..................... 600/30 X
4,994,020  2/1991  Polyak ........................ 600/31
5,013,292  5/1991  Lemay ........................ 600/30

FOREIGN PATENT DOCUMENTS 1174814  12/1969  United Kingdom ............ 623/14

Primary Examiner—David H. Willse
Attorney, Agent, or Firm—Peter C. Richardson; Lawrence C. Akers; Michael J. Pantuliano

[57] ABSTRACT

An implantable artificial sphincter system for reversibly occluding a body passageway, preferably the urethra, enables the body passageway to be opened and closed in sequence due to the action of a lifting and lowering device which is adapted to be in integral contact with or disposed about the body passageway. An actuating device is operably connected to the lifting and lowering device, and a pump capable of being volitionally operated is in fluid communication with the actuating device to provide a pressurized flow of fluid into the actuating device.

11 Claims, 3 Drawing Sheets

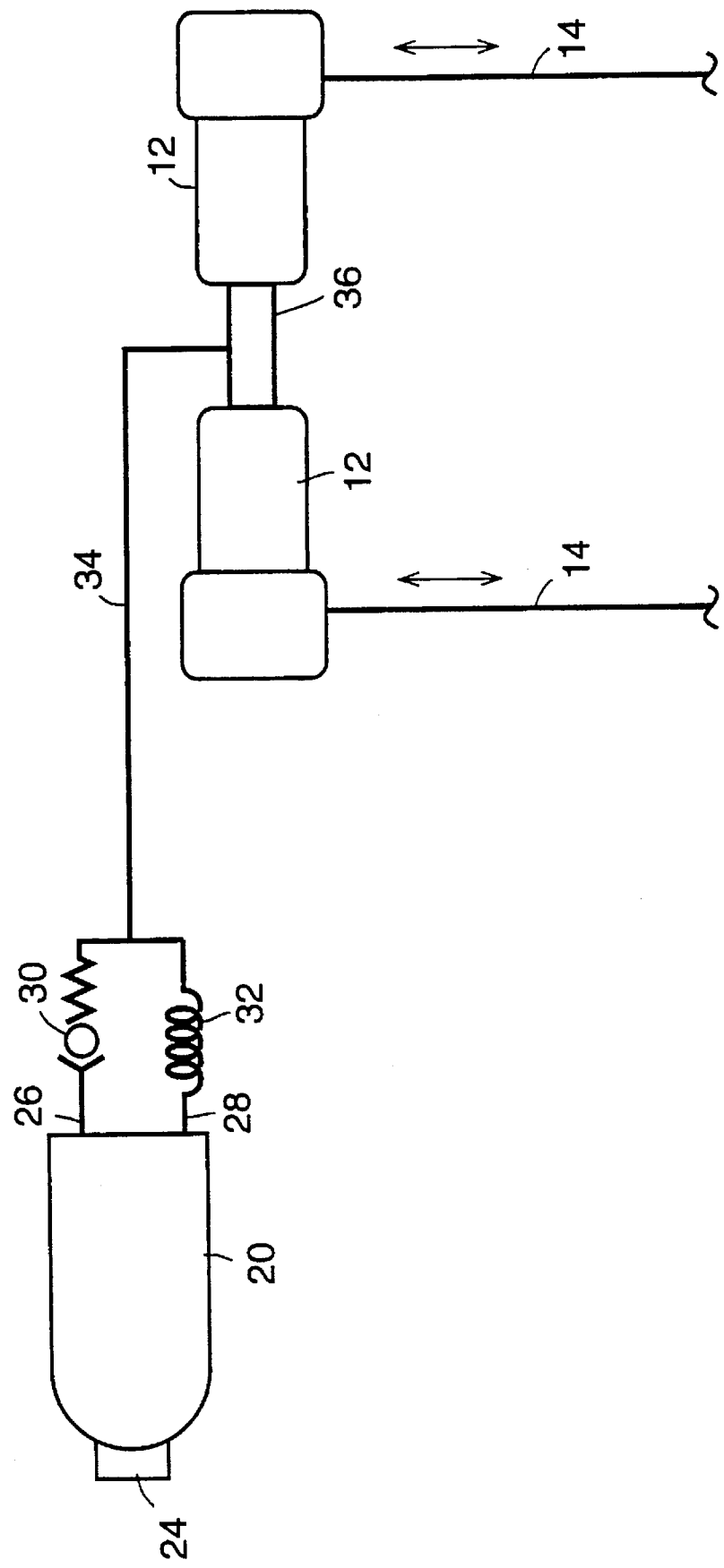

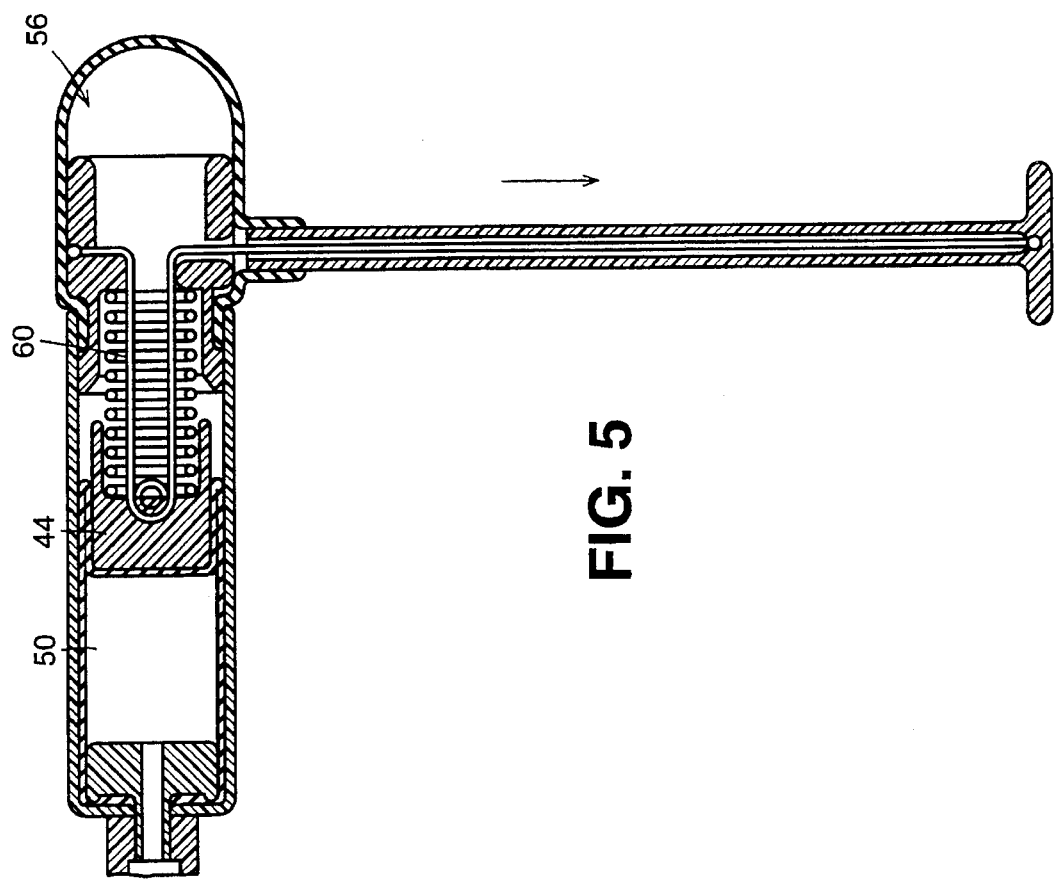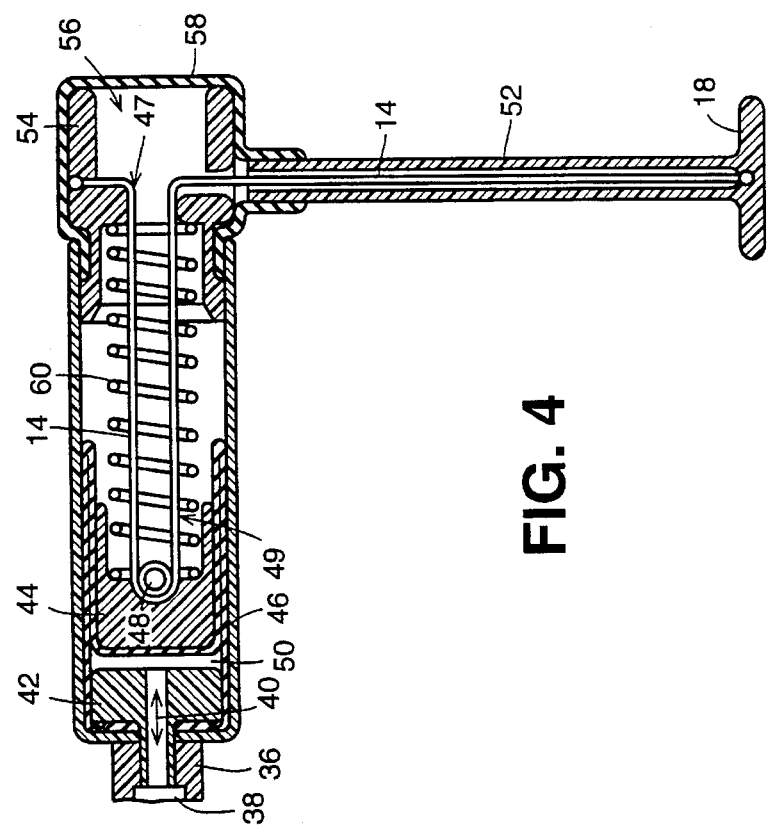

IMPLANTABLE SPHINCTER SYSTEM UTILIZING LIFTING MEANS

BACKGROUND OF THE INVENTION

This invention relates generally to an improved artificial sphincter system for the control of excretory body passages, and more specifically to a device and method for treating incontinency utilizing lifting means for reversibly occluding and/or repositioning said body passages.

The artificial sphincters for treating incontinence which are known or described in the art often employ a distally located fluid reservoir, usually of the balloon or bulb type, which in conjunction with one or more pumps serves to transfer fluid into or out of an inflatable cuff which is disposed about the body passageway to be occluded. When the cuff is inflated, the body passageway is occluded; when it is deflated the body passageway is opened and excretion occurs. It is also the norm that these basic components, that is, cuff, pump means, and reservoir are connected by means of lumens or fluid transmission passageways. Typically one fluid transmission passageway connects the cuff with the pump while a second transmission passageway connects the pump with the reservoir.

The location of the balloon type reservoirs are of particular concern in the known artificial sphincter systems. This is because reservoirs of this type tend to be rather large, particularly in proportion to the other components of the system. Because of their size, they are usually located in areas of the body which have room for such implantation. In most instances this will be in the abdomen. However, to implant bulb or balloon reservoirs in the abdomen necessitates rather complex surgery which can be debilitating particularly to the elderly. Moveover, abdominal surgery also incurs a fairly high risk of postoperative infection and is almost always rather long in duration, requiring a fairly lengthy postoperative healing period due to the trauma to which the body has been subjected. It is apparent that it would be highly desirable to avoid abdominal surgery and in general to reduce the complexity of the implantation procedures for artificial sphincters.

In order to prevent female urine incontinence the cuff or other occlusion means is usually disposed about the bladder neck, i.e. in the proximal vicinity of the urethra. In the case of males, the cuff is usually placed either about the bladder neck and the bulbous urethra. Using this type of device the urethra is physically closed by the pressure of the cuff. The natural method of maintaining continence does not involve compressive forces around the exterior of the urethra, but rather the lifting or dropping of the position of the bladder neck. The cuff devices tend to cause tissue damage (tissue necrosis) of the urethra wall. Particularly if a bladder is capable of reflective contraction, the cuff type artificial sphincter must be used with extreme care. To maintain the continent state in the face of increased vesicle pressure requires a very large compressive force around the urethra. The resulting forces can produce tissue damage to the patient. While this is not a common occurrence, when it does occur it can result in the need for a serious operation necessitating the removal of the cuff. Of course incontinence continues. Similarly the constricting efficiency of the cuff can be diminished significantly if the urethra wall occluded by the cuff begins to undergo necrosis and atrophy.

Another method of treating incontinence, particularly female stress incontinence, involves suspension of the bladder neck or, in the care of male patients suspension of the membranous urethra. The purpose of this suspension procedure is to achieve continence by lifting and fixating the position of the urethrovesical junction or proximal urethra to that point where the urethra is closed. A major problem encountered during these procedures is the difficulty in obtaining the correct positioning of the bladder neck or proximal urethra so that such positioning is sufficiently high to avoid incontinence without causing obstruction or urine retention.

In U.K. Patent No. 1,174,814 there was provided a device for the occlusion and release of an artificially constructed duct. A sling for this purpose is provided which is tightened by a mechanical device and is released by a spring. No lifting is involved.

U.S. Pat. No. 4,118,805 discloses a mechanical sphincter which may be adjusted after implantation. No sling or lifting action is proposed in the patent.

It would be very desirable to have a device whereby if a patient does not wish to void, or does not have to, he or she can raise the urethra or bladder neck by means of a device such as a sling to a point whereby continence is reasonably guaranteed, but wherein when there is a desire or need to void, he or she can lower the urethra or bladder neck voluntarily to a position where voiding can occur. If the need for a cuff can also be thereby alleviated, this would also be very advantageous.

It would also be desirable to provide an apparatus for maintaining continence which did not significantly damage the tissues of the bladder, urethra or surrounding areas.

SUMMARY OF THE INVENTION

The present invention relates to an implantable sphincter system for controlling incontinence in a human body at the volition of the patient, wherein means are provided for lifting or lowering a tubular passageway so that the passageway, hereinafter discussed with relation to the urethra, is reversibly occluded and when repositioned, is opened. Anchoring means can be provided which are attached to the lifting or lowering means to anchor the latter in place, and actuating means are provided which are also operably connected to the lifting or lowering means. When actuated on command, the actuating means will effect the raising or lowering of the lifting or lowering means to occlude or open the urethra.

In another embodiment of this invention, the lifting or lowering means can be attached to a sling which is positioned underneath the urethra or bladder neck. Attached to the sling are means such as depending cords which engage an actuator which will, on command, raise or lower the cords. As a consequence, the urethra or bladder neck will be raised or lowered by the action of the cords upon the sling. The position of the sling can be fixed, as predetermined, at a point within the body above which the urethra will be occluded and below that at which the urethra will be opened. In the occluded position, the involuntary passage of urine through the urethra is prevented, or at least greatly inhibited.

In operation, the actuator, as hereinafter defined, raises or lowers the cords on command, preferably as a voluntary act of the patient. As a consequence the patient can decide when he or she should void. Continence is reasonably guaranteed when the urethra or bladder neck is in a predetermined (and normal) raised position. However, when the patient feels the need to void he or she can voluntarily lower the bladder neck or urethra to a predetermined position permitting urine to flow freely.

BRIEF DESCRIPTION OF THE DRAWINGS

FIG. 3 is a schematic view of an actuator control mechanism, shown with actuators and depending cords, of an implantable sphincter system according to the subject invention.

FIG. 4 is a side elevational view indicating the disposition of the components of a preferred actuator of the implantable sphincter of the subject invention, in conjunction with cords and anchors, when the sphincter is in a raised, continent mode.

FIG. 5 is a side elevational view according to FIG. 4, indicating the disposition of the components of the actuator when the sphincter is in a lowered, voiding mode.

DETAILED DESCRIPTION OF THE DRAWINGS

Figure 1:
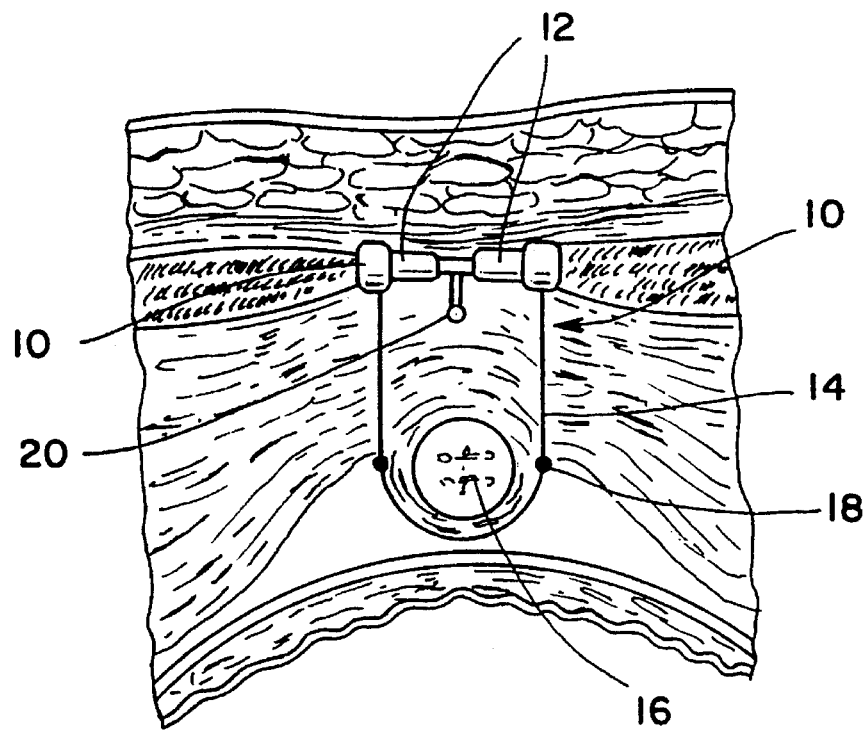
FIG. 1 is a sectional view, in simplified form, of the lower abdomen of a human female, indicating the environmental placement of an implantable sphincter according to the subject invention, utilizing anchors attached to the urethra, and cords as the lifting means.

In the drawings like reference numerals are utilized for like pads throughout the respective views. In FIG. 1 there is illustrated, in simplified form, a sectional view of an implantable sphincter system 10 according to the subject invention, disposed within the environment of a lower abdomen of a human female. The sphincter system as shown includes actuators 12 as hereinafter defined. Depending downward from the actuators in the sectional view are cords 14 which in this environment are fastened to the outer walls of a urethra 16, by means of anchors 18. Pump 20 is shown communicating with actuators 12.

Figure 2:
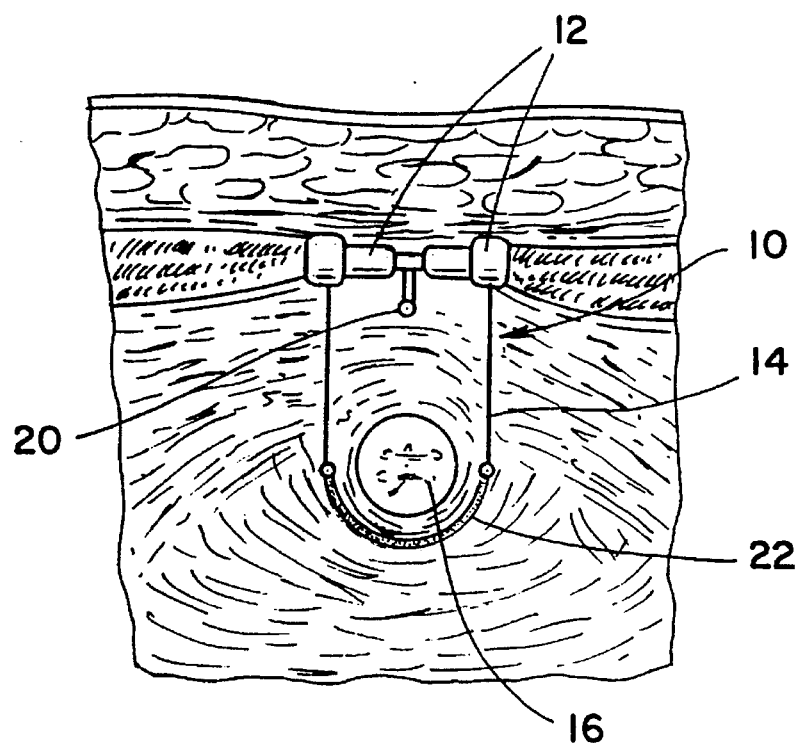
FIG. 2 is sectional view of another embodiment of the subject invention in a human male showing a sling adapted to be disposed about the urethra.

In FIG. 2 there is illustrated a sectional view of the sphincter system 10, which is identical in every aspect to FIG. 1, except that it is indicated as being disposed in the lower abdomen of a human male, and employs, as the lifting means, a sling 22 in place of anchors 18.

In FIG. 3 there is shown a schematic view of the implantable sphincter system of the subject invention. As indicated, an actuator control mechanism includes a septum 24 for receiving or removing fluid. The septum 24 is at the proximal end of pump 20. Extending outwardly from the distal end of pump 20 and in fluid connection therewith are a pair of fluid passageways 26 and 28 which are substantially parallel to each other. Along upper passageway 26 is check valve 30. Along lower passageway 28 is resistor 32. Both passageways 26 and 28 are in fluid communication at the distal end with tubing or passageway 34. The latter passageway 34 extends into and is in fluid communication with actuators 12, which are mirror images of each other through connector 36. Depending downwardly from each of the actuators are the cords 14 shown in FIGS. 1 and 2.

The septum and pump bulb in females are preferably placed in the labia for easy manipulation by the patient or other persons. In males the septum and pump bulb are preferably placed in the scrotum.

FIG. 4 depicts a side elevational view of a typical actuator of the implantable sphincter system of this invention when the sphincter is in its normal, i.e. continent, mode. As stated there would normally be two actuators which would be mirror images of each other. Less preferably one actuator could be employed.

At the extreme proximal end of the actuator is orifice 38 which is in fluid communication with the connector 36 (shown in FIG. 3). Orifice 38 permits fluid to flow into the actuator through passageway 40, the distal end of which exits into chamber 50. Disposed about passageway 38 is plug 42. Rolling diaphragm 46 is proximal to and disposed about plunger 44 and is integral with chamber 50. Plug 42 fixes the proximal end of the rolling diaphragm 46 and seals the inlet part of the actuator.

An integral part of the plunger 44 is roller 48 about which is cord 14, the latter extending laterally through the actuator in parallel paths 47 and 49. The lower path 49 exits from the actuator in a depending direction terminating with anchor 18, which is fixed in any suitable way to the urethra or the bladder neck. The depending cord 14 is defined within outer tubing 52. The upper path 47 of the cord 14 is fixed to the sleeve 54 of the reservoir 56 which includes in its distal portion distensible diaphragm 58. Defined along the lateral route of both paths of the cord 14 is spring 60 which in the continent mode is in a substantially compressed state. The compression force of the spring 60 keeps the plunger 44 in a proximal position.

In FIG. 4 plunger 44 is in its extreme position proximal to the chamber 50 and plug 42. As a consequence depending cord 14 and anchor 18 are also in their maximum raised position as are the urethra and bladder neck (not shown) which are raised above the level predetermined to occlude the urethra, i.e. to provide continence. While the weight of the urethra or bladder neck tends to exert a pulling force on the cord in a downward direction, the force exerted by spring 60 in its non-compressed state keeps the plunger in its proximal position and the urethra in a raised position.

It should be noted that fluid is contained in all the passageways, chambers and spaces of the actuator. As explained below, to achieve the voiding mode this fluid will be pressurized. Since fluid (which in this device is normally a liquid), cannot be compressed, outer reservoir 56 contains in its distal position a flexible diaphragm 58 which is capable of ballooning outwardly in a lateral direction to accommodate the volume change caused by the lateral motion of the plunger. It should also be noted that the displacement of the cord 14 is double that of plunger 44 because of the cord path about roller 48. This fact enables the cord and anchor to move downwardly for a greater distance than the movement of the plunger with the roller, this all being accomplished with only a small displacement of fluid, i.e., from the pump to chamber 50.

FIG. 5 depicts a typical actuator of the implantable sphincter system of the invention in the lowered, voiding mode. As will be explained below, the force of pressurized fluid in chamber 50 has resulted in plunger 44 moving in a distal direction, causing spring 60 to be compressed thereby lowering cord 14 and anchor 18. As a consequence the urethra is opened and the patient can void. Outer reservoir 56 has ballooned in a lateral direction to accommodate the passage of the pressurized fluid. However, as stated above, only a small volume of fluid is necessary to achieve the desired positioning of anchor 18 so as to open the urethra, particularly since the aforementioned weight of the urethra tends to encourage the orientation of the anchors in a downward depending direction.

Before implanting the device of this invention, a doctor initially determines where the urethra should be positioned in the abdomen to achieve continence.

After implanting the device, the doctor activates the device by squeezing the pump 20. Pressurized fluid exits from the pump into passageway 26 through check valve 30 and then by passageway 34 into connector 36. The pressurized fluid then continues through connector 36 into the actuator through orifice 38 into passageway 40. The pressurized fluid then increases the pressure of the fluid in chamber 50 which in turn increases the pressure in front of the rolling diaphragm 46 and the plunger 44. This forces the plunger in a distal direction, thereby compressing the spring 60. There is therefore, no tension on the cords 14 which are thereby lowered along with the anchor 18 which is fastened to the urethra. (As indicated above, a sling can be used in place of an anchor), The natural inclination of the urethra to move downward facilitates this movement until the urethra is open and urination can occur freely.

During the voiding stage, pressurized fluid in chamber 50 starts to move back into the pump bulb through passageway 34 and resistor 32. The resistor slows the passage of fluid, i.e. acts as a time delay. This permits the patient to have enough time to empty his or her bladder. The diminished pressure in chamber 50 allows the force exerted by the compressed spring to slowly push the plunger in a proximal direction, i.e. back to the original, continent position. As a consequence, cord 14 is raised along with the urethra or bladder neck so that the latter reassumes its predetermined continent position.

It is an advantage of this invention, therefore, that a patient can volitionally void when desired, followed by an automatic resumption of the continent position.

It should be noted that the purpose of the septum 24 placed on the proximal portion of the pump 20 (shown in FIG. 3) is to allow a doctor to adjust the predetermined position of the anchor along with the bladder neck or the urethra after surgery. This can be accomplished by puncturing the septum with a suitable needle attached to a syringe. By changing the volume of the liquid in the pump the predetermined position of the urethra can be adjusted continuously after surgery, as desired. In effect, by adding a small volume of liquid the position of the urethra can be lowered; by decreasing liquid the position of the urethra can be raised.

It is apparent that modifications and variations besides those specifically mentioned may be made in the structures and techniques described herein and depicted in the accompanying drawings, without departing from the concept of the present invention.

I claim:

1. An implantable sphincter system for reversibly occluding and opening a tubular passageway of a human body, which comprises, lifting and lowering means comprising a spring operated cord adapted to be in integral contact with or disposed about the tubular passageway, which when raised to a predesignated position within the human body will occlude the passageway and when lowered below said position will open the passageway;

positioning means integral with said lifting and lowering means to position said lifting and lowering means, as desired;

actuating means operably connected to said lifting and lowering means;

pump means capable of being volitionally operated, said means being in fluid communication with, and capable of supplying pressurized fluid to said actuating means, wherein when said pressurized fluid is applied to said actuating means, said lifting and lowering means are lowered to the position wherein the body passageway assumes an open mode; and, time delay means disposed between said pump means and said actuating means to sequentially enable a reverse pressurized liquid flow to cause the lifting and lowering means to return automatically to the predetermined raised position, and the passageway to an occluded mode.

2. A system according to claim 1, wherein the tubular passageway is the urethra.

3. A system according to claim 2, wherein the positioning means is an anchor or a sling.

4. A system according to claim 3, wherein the time delay means is a resistor.

5. An implantable sphincter system for reversibly occluding and opening a urethra, which comprises, lifting and lowering means adapted to be attached to or about the urethra, said means comprising a cord, the lower portion of which depends downward from an actuator, wherein, when said cord is in an elevated predetermined position within the human body the urethra will be occluded, and when lowered below said position the urethra will be opened;

said actuator including a spring about which is defined an upper portion of said cord;

pump means capable of being volitionally operated from outside the body, said pump means being in fluid communication with, and capable of supplying fluid under pressure to said actuator whereby when said pressurized fluid is applied to said actuator said spring is compressed thereby lowering the depending portion of the cord to the position wherein the urethra assumes an open, voiding mode; and time delay means between said pump means and actuator to sequentially enable a reverse pressurized liquid flow to cause the cord to return automatically to the predetermined elevated position, and the urethra to the occluded mode.

6. A system according to claim 5, wherein positioning means are provided, said means being an anchor adapted to be fastened to the urethra, or a sling adapted to be disposed about the urethra.

7. A system according to claim 6, wherein the time delay means is a resistor.

8. A system according to claim 7, wherein proximal to said pump means is a septum for enabling fluid to be introduced into the pump means, which enables the liquid of the system to be adjusted continuously, as needed.

9. A system according to claim 8, wherein when the volume of the liquid is increased the position of the urethra can be lowered and when decreased the position of the urethra can be raised.

10. A system according to claim 8, wherein a reservoir containing a flexible diaphragm is disposed on a distal end of the actuator, said flexible diaphragm being capable of ballooning as a consequence of the force of the pressurized fluid emanating from the pump means.

11. A system according to claim 8 wherein said septum and pump means are adapted to be placed in the labia for females, and in the scrotum for males.

* * * * *